United States Patent [19]
Brooks et al.

[11] Patent Number: 5,304,157
[45] Date of Patent: Apr. 19, 1994

[54] MEDICO-SURGICAL COLLECTION BAGS

[75] Inventors: Kenneth J. Brooks, Lancing; David Cross, Rustington, both of England

[73] Assignee: Smiths Industries Public Limited Company, London, England

[21] Appl. No.: 32,320

[22] Filed: Mar. 17, 1993

[30] Foreign Application Priority Data

Mar. 28, 1992 [GB] United Kingdom ............. 9207007

[51] Int. Cl.$^5$ .............................................. A61F 5/44
[52] U.S. Cl. .................................. 604/333; 604/344
[58] Field of Search .......................... 604/332-345; 128/905

[56] References Cited
U.S. PATENT DOCUMENTS

| | | | |
|---|---|---|---|
| 4,460,392 | 7/1984 | Poulsen et al. | 604/333 |
| 4,723,951 | 2/1988 | Steer | 604/333 |
| 4,938,749 | 7/1990 | Jensen | 604/333 |
| 5,085,652 | 2/1992 | Johnson et al. | 604/333 |
| 5,167,650 | 12/1992 | Johnsen et al. | 604/333 |

FOREIGN PATENT DOCUMENTS

| | | |
|---|---|---|
| 2083760 | 3/1982 | United Kingdom . |
| 2213728 | 8/1989 | United Kingdom . |
| 2227668 | 8/1990 | United Kingdom . |
| 2247840 | 3/1992 | United Kingdom . |

*Primary Examiner*—Randall L. Green
*Assistant Examiner*—Rob Clarke
*Attorney, Agent, or Firm*—Pollock, VandeSande and Priddy

[57] ABSTRACT

An ostomy bag has a non-adhesive filter formed by a carbon fabric disc with impermeable layers on the front and back surfaces. The front layer has a central aperture whereas the rear layer is imperforate. The filter is releasably secured to an adhesive area around a vent opening of the bag with the aperture aligned with the opening so that gas can flow into the filter and radially outwards. The filter be peeled off and reversed to block escape of gas from the opening.

15 Claims, 2 Drawing Sheets

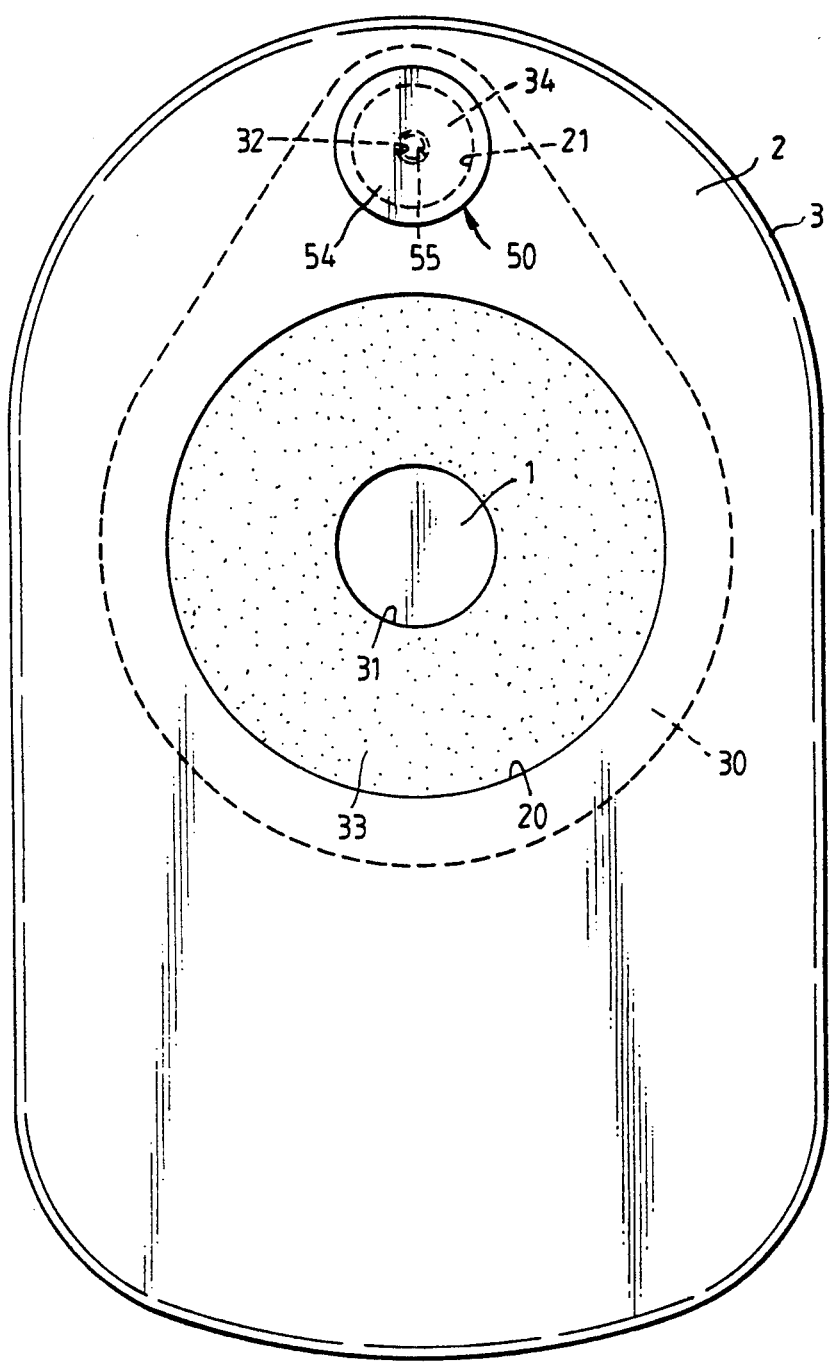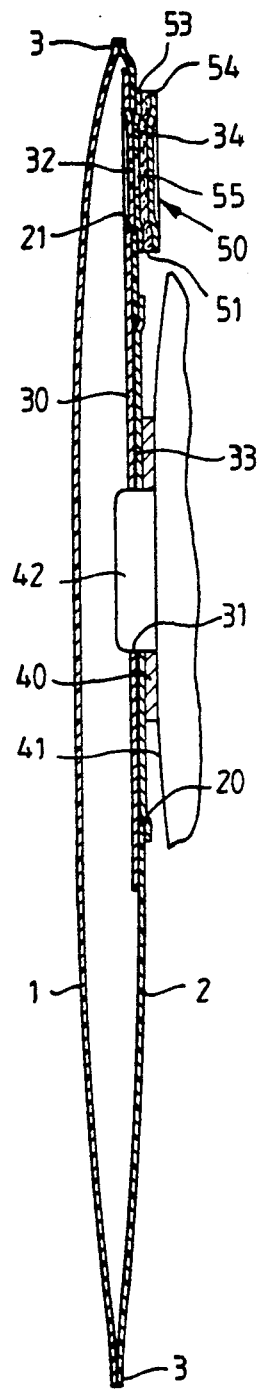

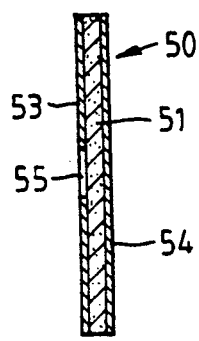
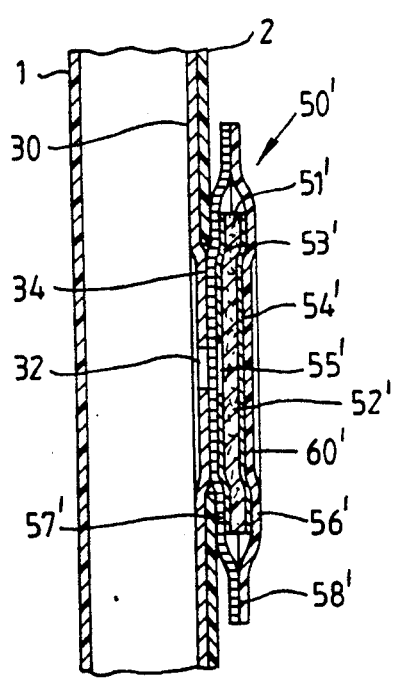
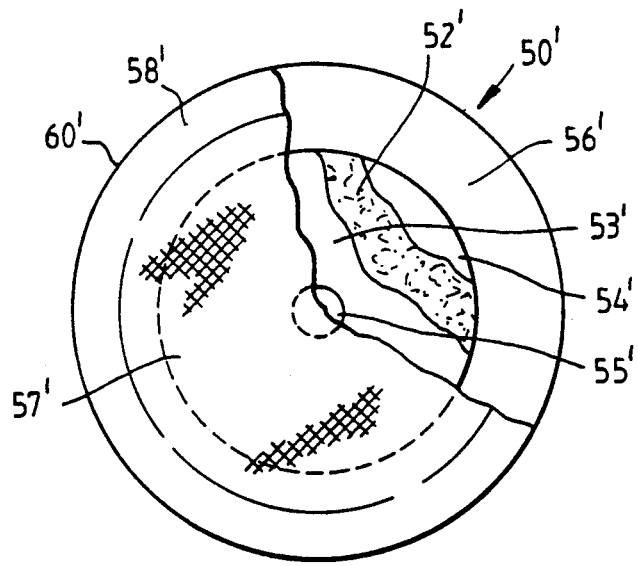

MEDICO-SURGICAL COLLECTION BAGS

BACKGROUND OF THE INVENTION

This invention relates to medico-surgical collection bags.

The invention is more particularly concerned with filtered bags, such as ostomy bags.

An ostomy bag comprises a bag of flexible plastics material sealed around its edge and having an opening in one face which, in use, is secured around the user's stoma so that discharged material enters the bag. The most convenient way of attaching the bag to the patient is by means of an adhesive region around the bag opening which adheres directly either to the patient's skin or to the front of a separate patient fitment which is secured to the skin. In GB2213728 there is described a bag in which a flange with an adhesive surface is secured to the inside surface of a wall of the bag around its opening, and in which the opening in the wall exposes adhesive on the flange. An external flange is secured to the exposed adhesive region and this is used to secure the bag to the patient. In GB 2247840 there is described a two-part bag assembly in which the bag is adhered to a separate patient fitment.

It is common practice for such bags to have a filtered vent to allow for the escape of gas from the bag, the filter reducing the transmission of ordors. Preferably, the vent should be capable of being completely sealed so that a cushion of gas can be trapped in the bag. This is sometimes necessary to prevent the accumulation of faeces around the stoma and to keep the front wall of the bag away from the stoma to reduce irritation of the stoma.

BRIEF SUMMARY OF THE INVENTION

It is an object of the present invention to provide an improved medico-surgical collection bag.

According to one aspect of the present invention there is provided a medico-surgical collection bag having a front wall, a rear wall, a first opening through which discharged material from the user enters through the rear wall of the bag, a vent opening through which gas can escape from the bag, an adhesive area around the vent opening and a filter that can filter gas escaping from the bag, the filter including a disc-shape filter element having a first region that allows passage of gas into the filter element and a second region which is substantially non-permeable, and both regions of the filter being releasably securable to the adhesive area such that when the first region is secured to the adhesive area gas can escape through the vent opening into the filter element and pass outwardly through the filter element, and such that when the filter is displaced and the second region is secured to the adhesive area, gas flow through the vent opening is blocked.

The first region is preferably provided on one side of the filter element, the second region being provided on the opposite side of the filter element.

According to another aspect of the present invention there is provided a medico-surgical collection bag having an opening through which discharged material from the user enters the bag, a vent opening through which gas can escape from the bag, an adhesive area around the vent opening and a filter that can filter gas escaping from the bag, the filter including a disc-shape filter element having one side that allows passage of gas into a central region of the filter element, a layer of substantially non-permeable material on the opposite side of the filter element, and both sides of the filter being releasably securable to the adhesive area such that when one side is secured to the adhesive area gas can escape through the vent opening into the central region of the filter element and pass radially outwardly through the filter element, and such that when the filter is reversed and the other side is secured to the adhesive area, gas flow through the vent opening is blocked by the layer of non-permeable material.

The filter element may have a layer on the one side of substantially non-permeable material with an aperture therethrough that is aligned with the vent opening. The filter element is preferably of circular shape, the aperture in the layer on the one side being located centrally. The filter element may be provided by a carbon fabric disc. The bag may include a flange secured to the inside surface of the rear wall, the flange having an opening providing the vent opening of the bag, the rear wall having an aperture larger than the opening in the flange and the adhesive area being provided on the flange around its opening so that it is exposed within the aperture in the rear wall. The flange may provide an adhesive area around the opening of the bag through which discharged material enters the bag. The filter may include an outer envelope comprising a first disc of material that is permeable through its thickness which extends across and overlaps the filter element on one side and a second disc which extends across and overlaps the filter element on the other side, the two discs being sealed together around their edge.

An ostomy bag according to the present invention will now be described, by way of example, with reference to the accompanying drawings.

BRIEF DESCRIPTION OF THE DRAWINGS

FIG. 1 is an elevation view of the rear side of the bag;

FIG. 2 is a sectional side elevation of the bag;

FIG. 3 is an enlarged sectional side elevation of the filter of the bag;

FIG. 4 is an enlarged sectional side elevation of a part of an alternative bag showing its filter; and FIG. 5 is an elevation view of the front side of the filter of FIG. 4.

DETAILED DESCRIPTION OF THE PREFERRED EMBODIMENT

With reference to FIGS. 1 to 3, the ostomy bag comprises two sheets or walls 1 and 2 of flexible plastics material, such as polyvinylidene chloride, welded together around their outer edge 3 to form a closed bag which is about 200 mm long and about 130 mm wide.

The rear wall 2 has two circular apertures 20 and 21 located one above the other. The lower aperture 20 is about 75 mm in diameter and its center is located about 75 mm from the top of the bag. The upper aperture 21 is about 18 mm in diameter with its center being located about 20 mm from the top of the bag and about 55 mm from the centre of the lower aperture 20.

Secured to the inner surface of the rear wall 2 is a flange 30 made of a plastics material such as polypropylene. The flange 30 is flexible but is less flexible and more resilient than the bag walls 1 and 2, being about 0.06 mm thick and of pear shape. The flange 30 extends over the apertures 20 and 21, being slightly wider at its lower end than the lower aperture 20, and being slightly wider at its upper end that the upper aperture 21. Two openings 31 and 32 in the flange 30 lie centrally within the apertures 20 and 21 respectively. The diameter of the lower opening 31 is typically about 25 mm but could range in size from 10 mm to 60 mm according to the size of the stoma with which the bag is used. The diameter of the upper opening 32 is about 2.5 mm. The rear surface of the flange 30, in contact with the rear wall 2, is adhesive so that it provides two adhesive annular areas 33 and 34 respectively within the apertures 20 and 21 of the rear wall.

The adhesive area 33, within the lower aperture 20, is used to secure the bag to a conventional patient fitment 40 attached to the patient's skin 41 around a stoma 42 (FIG. 2). In this way, the lower opening 31 in the flange 30 provides the opening through which discharged material from the stoma enters the bag.

The adhesive area 34, within the upper aperture 21, is used to secure a flexible, circular filter 50 to the bag, the upper opening 32 providing a gas vent opening for the bag.

The filter 50 comprises a filter element 51 in the form of a conventional activated carbon fabric disc which is about 23 mm in diameter and about 1 mm thick. The filter 50 also has respective layers 53 and 54 of a thin, non-permeable plastic fixed by means of adhesive or heat welding to the forward and rearward surfaces of the disc 51. The forward layer 53 has a central aperture 55 about 4 mm in diameter; the rear layer 54 is imperforate. The edge of the disc 51 is exposed, that is, it is not covered by either layer 53 or 54.

In normal use, as shown, the filter 50 is secured to the bag with a first region provided by the forward layer 53 attached to the adhesive area 34, with the aperture 55 overlying the opening 32. Gas flowing out of the bag through the opening 32 will flow through the aperture 55 in the layer 53 and into the filter element 51. There will not be any significant flow of gas in the plane of the layer 53 laterally between the rear wall 2 and the filter 50 because the adhesive area 34 forms a seal around the aperture 55 in the layer 53. Axial flow of gas through the element 51 is prevented by the non-permeable rear layer 54 so that it flows radially outwardly to the edge of the filter element. The rear layer 54 could have a ring of holes around its periphery to facilitate gas passage through the filter element and so that gas still flowed radially.

The nature of the adhesive on the flange 30 and the material of the layers 53 and 54 on the filter 50 are such that it can be peeled away from the adhesive and reapplied as necessary. In normal use, the filter 50 is attached to the bag in the manner described so that gas in the bag can vent through the filter. If desired, the filter 50 can be turned back-to-front and so that a second region provided by the non-permeable layer 54 on the other side of the filter is secured to the adhesive region 34 and the opening 32 is completely blocked. In this way, a cushion of gas can be trapped in the bag to reduce accumulation of faeces around the stoma and reduce contact of the front wall 1 of the bag with the stoma 42. If gas should build up excessively in the bag, the filter 50 can be removed completely to allow as much venting as required, and subsequently be replaced.

Manufacture of the bag is considerably simplified by the fact that the adhesive region around both the vent opening 32 and the bag opening 31 is provided on the same flange 30. The bag can have a very low profile and be flexible, so that it remains unobtrusive beneath the user's clothing. Because the adhesive for securing the filter assembly is provided on a flange in the bag rather than on the filter assembly, there is less risk that repeated removal of the filter assembly will damage the bag wall as could be the case if an adhesive filter assembly were attached directly to the bag wall.

Where the bag is not used with a patient fitment but is instead secured directly to the user's skin, a separate external flange is preferably secured to the adhesive region 33 on the internal flange 30, in the manner described in GB 2213728.

Various modifications are possible. For example, instead of reversing the filter, it could be peeled off and replaced the same way around but with the aperture 55 displaced so that a non-permeable region of the layer 53 covers the opening 32 in the bag. In another modification a filter element 51' could be enclosed within an outer envelope 60' as shown in FIGS. 4 and 5, to form a filter assembly 50'. The envelope 60' is provided by two outer polythene discs 56' and 57' which are both larger than the filter element 51', being about 35 mm in diameter. The two discs 56' and 57' are joined together by a weld 58' close to their edge so that the filter element 51' is trapped between them. The rear disc 56' is imperforate and is substantially non-permeable. By contrast, the forward disc 57' is perforated with holes over its entire surface so that it is permeable through its thickness and gas can flow freely through the disc. The nature of the disc 57' is such that, although gas can flow through its thickness, no gas can flow along the plane of the disc, laterally between the filter element 51' and the rear wall 2 of the bag. In this embodiment, the permeable, forward disc 57' is secured to the non-permeable layer 53', over its surface, by welding or adhesive; the rear disc 56' is not directly attached to the filter element 51'. The discs 56' and 57' are flexible so that they form a flexible envelope and, since the filter element 51' is flexible, the filter assembly 50' as a whole is flexible. In use, the forward disc 57' is attached to the adhesive region 34 with the aperture 55' overlying the opening 32. Gas flowing out of the bag through the opening 32 will flow through the thickness of the forward disc 57', through the aperture 55' in the layer 53' and into the filter element 51'. As in the first embodiment, the filter assembly 50' can be peeled off the adhesive 34 to allow unfiltered venting, and or turned back-to-front so that the non-permeable disc 56' is secured to the adhesive, blocking the opening 32.

What we claim is:

1. A medico-surgical collection bag comprising: a rear wall; a front wall sealed around an edge to the rear wall; a first opening by which discharged material from a user enters through the rear wall of the bag; a second, vent opening through which gas can escape from the bag; an adhesive area around the vent opening; and a non-adhesive filter that can filter gas escaping from the bag, the filter including a disc-shape filter element, said filter element being selectively displaceable between a first position in which a gas permeable first region of the filter is releasably secured to the adhesive area in overlay relation to the vent opening to allow passage of gas into the filter element so that gas can escape from the bag through the vent opening into the filter element and pass outwardly through the filter element, and a second position in which a non-permeable second region of the filter is releasably secured to the adhesive area in overlay relation to the vent opening to block gas flow from the bag through the vent opening.

2. A medico-surgical bag according to claim 1, wherein the first region is provided on one side of the filter element, and wherein the second region is provided on an opposite side of the filter element.

3. A medico-surgical bag according to claim 2, wherein the filter element has a layer on the one side of substantially non-permeable material with an aperture therethrough that can be aligned with the vent opening to allow escape of gas through the filter element.

4. A medico-surgical bag according to claim 3, wherein the filter element is of circular shape and the aperture in the layer on the one side is located centrally.

5. A medico-surgical bag according to claim 1, wherein the filter element is provided by a carbon fabric disc.

6. A medico-surgical bag according to claim 1, wherein the bag includes a flange with an opening and means securing the flange to an inside surface of the rear wall, wherein the opening in the flange provides the vent opening of the bag, wherein the rear wall has an aperture therethrough larger than the opening in the flange, and wherein the adhesive area is provided on the flange around its opening so that it is exposed within the aperture in the rear wall.

7. A medico-surgical bag according to claim 6, wherein the flange extends around the first opening of the bag through which discharged material enters the bag, and wherein the adhesive on the flange provides an adhesive area around the first opening.

8. A medico-surgical bag according to claim 1, wherein the filter includes an outer envelope comprising a first disc, the first disc being permeable through its thickness and extending across and overlapping the filter element on one side, a second disc, the second disc extending across and overlapping the filter element on the other side, and means sealing the two discs together around their edge.

9. A medico-surgical collection bag comprising: a rear wall; a front wall secured around an edge to the rear wall; a first opening by which discharged material from a user enters through the rear wall of the bag; a second vent opening through which gas can escape from the bag; an adhesive area around the vent opening; and a non-adhesive filter that can filter gas escaping from the bag, wherein the filter includes a disc-shape filter element having one side that allows passage of gas into a central region of the filter element, a layer of substantially non-permeable material on an opposite side of the filter element, and wherein both sides of the filter are releasably securable to the adhesive area such that when one side is secured to the adhesive area gas can escape through the vent opening into the central region of the filter element and pass radially outwardly through the filter element, and such that when the filter is reversed and the other side is secured to the adhesive area, gas flow through the vent opening is blocked by the layer of non-permeable material.

10. A medico-surgical bag according to claim 9, wherein the filter element has a layer on the one side of substantially non-permeable material with an aperture therethrough that is aligned with the vent opening.

11. A medico-surgical bag according to claim 10, wherein the filter element is of circular shape and the aperture in the layer on the one side is located centrally.

12. A medico-surgical bag according to claim 9, wherein the filter element is provided by a carbon fabric disc.

13. A medico-surgical bag according to claim 9, wherein the bag includes a flange with an opening and means securing the flange to an inside surface of the rear wall, wherein the opening in the flange provides the vent opening of the bag, wherein the rear wall has an aperture therethrough larger than the opening in the flange, and wherein the adhesive area is provided on the flange around its opening so that it is exposed within the aperture in the rear wall.

14. A medico-surgical bag according to claim 13, wherein the flange extends around the first opening of the bag through which discharged material enters the bag, and wherein the adhesive on the flange provides an adhesive area around the first opening.

15. A medico-surgical collection bag comprising: a rear wall; a front wall secured around an edge to the rear wall; a first aperture in the rear wall through which discharged material from a user enters through the rear wall of the bag; a second aperture in the rear wall located above the first aperture and through which gas can escape from the bag; an adhesive flange secured to the inside of the rear wall, the flange extending across the first and second apertures so as to expose respective adhesive areas within the first and second apertures and the flange having two openings therethrough located centrally within the first and second apertures respectively; and a filter that can filter gas escaping from the bag, wherein the filter includes a disc-shape filter element having a layer of substantially non-permeable material on each side, the layer on one side having an aperture therethrough that allows passage of gas into a central region of the filter element, and wherein both sides of the filter are releasably securable to the adhesive area within the second aperture such that when one side is secured to the adhesive area gas can escape through the second opening in the flange into the central region of the filter element and pass radially outwardly through the filter element, and such that when the filter is reversed and the other side is secured to the adhesive area, gas flow through the second aperture is blocked by the layer of non-permeable material.

* * * * *